US006780886B2

(12) United States Patent
Kondo et al.

(10) Patent No.: US 6,780,886 B2
(45) Date of Patent: Aug. 24, 2004

(54) ANTIOXIDANT CONTAINING VITAMIN E METABOLITE

(75) Inventors: Kazuo Kondo, Tokyo (JP); Osamu Igarashi, Tokyo (JP); Chikako Kiyose, Saitama (JP); Hiroyuki Yoshimura, Ibaraki (JP); Shigehiro Yoshitake, Nara (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 09/963,365

(22) Filed: Sep. 27, 2001

(65) Prior Publication Data

US 2002/0040053 A1 Apr. 4, 2002

(30) Foreign Application Priority Data

Sep. 27, 2000 (JP) ........................................ 2000-294802

(51) Int. Cl.[7] ......................... A61K 31/352; A61P 9/10
(52) U.S. Cl. ...................................... 514/456; 514/824
(58) Field of Search ........................................ 514/456

(56) References Cited

U.S. PATENT DOCUMENTS 5,821,264 A    10/1998    Lane et al.

FOREIGN PATENT DOCUMENTS

| WO | WO 96/16957 | 6/1996 |
| WO | WO 00/35444 | 6/2000 |

OTHER PUBLICATIONS

Simons et al. 1996, "What dose of vitamin E is required to reduce suseptibility of LDL to oxidation?", Australian and New Zealand Journal of Medicine, vol 26 no 4, p. 496–503.*

Christien et al. 1997, "gamma–tocopherol traps mutagenic electrophiles . . . ", Proceedings of the National Academy of Sciences, vol 94, p. 3217–3222.*

Schultz et al. 1995, "Novel urinary metabolite of alpha–tocopherol . . . ", American Journal of Clinical Nutrition, vol 62 supp 6, p. 1527S–1534S.*

Darko et al. 1997, "Endogenous Natriuretic Factors 6: The Stereochemistry of a Natriuretic gamma–tocopherol Metabolite LLU–alpha", vol 282 no 2, p. 648–656.*

HerbiesNaturals [online], [retrieved on Nov. 15, 2001]. Retrieved from the internet: <URL: http;//www.herbiesnaturals.com/search/show.php3?id=1168>, p. 1.*

US Trademark 2169587 [online], [retrieved on Nov. 14, 2001]. Retrieved from the internet:<URL: http://tess.uspto.gov/bin/gatexexe?f=doc&state=imfbnv.2.12, p. 1.*

Saldeen et al., J. of Amer. Coll. of Cardiology, vol. 34, No. 4, pp. 1208–1215, (1999).

Porkkala–Sarataho et al., Arterioscler Thromb. Vasc. Biol., vol. 20, No. 9, pp. 2087–2093, (2000).

Suarna et al., Biochimica Et. Biophysica Acta., vol. 1166, No. 2–3, pp. 163–170, (1993).

Jiang et al., PNAS, vol. 97, No. 21, pp. 11494–11499, (2000).

Stahl et al., Anal. Biochem., vol. 275, pp. 254–259, (1999).

* cited by examiner

Primary Examiner—Edward J. Webman
(74) Attorney, Agent, or Firm—Birch, Stewart, Kolasch & Birch, LLP

(57)    ABSTRACT

The present invention provides a method of preventing or treating a disease caused by oxidation in vivo by administering a pharmacologically effective amount of at least one compound selected from the group consisting of: (1) 2,5,7, 8-tetramethyl-2-(β-carboxyethyl)-6-hydroxychromane; and (2) 2,7, 8-trimethyl-2-(β-carboxyethyl)-6-hydroxychromane. Further, it provides use of a compound selected from the group consisting of (3) α-tocopherol, (4) α-tocotrienol, (5) γ-tocopherol and (6) γ-tocotrienol for generation in vivo of any of the above compounds (1) and (2) to treat a disease caused by oxidated low density lipoprotein (LDL).

2 Claims, 1 Drawing Sheet

Mean±SD (n=8), *p<0.05, **p<0.01 (t-test)

Mean±SD (n=8), *p<0.05, **p<0.01 (t-test)

ANTIOXIDANT CONTAINING VITAMIN E METABOLITE

FIELD OF THE INVENTION

The present invention relates to a vitamin E metabolite which exhibits anti-oxidant action and belongs to the field of food and pharmaceuticals.

PRIOR ART

Tocopherol and tocotrienol are known to have anti-oxidant action.

On the other hand, carboxyethylhydroxychromanes are in vivo metabolites of tocopherol and tocotrienol. Among all, 2,7,8-triethyl-2-(β-carboxyethyl)-6-hydroxychromane is known to have natriuretic activity (Wechter et al., Proc. Natl. Acad. Sci. USA, 93, 6002–6007, 1996) but other activities thereof are still unknown.

It has been suggested that α-tocopherol has anti-oxidant action to inhibit LDL (low density lipoprotein) oxidization which may possibly prevent crisis of arterial sclerosis. On the other hand, it has not been determined yet whether its analogues such as γ-tocopherol and tocotrienol have in vivo anti-oxidant action or not, since little of them could be detected in unchanged forms in blood after oral administration.

DISCLOSURE OF THE INVENTION

After examining the activities of carboxyethylhydroxychromane, (in vivo metabolites of tocopherol and tocotrienol), the present inventors unexpectedly found that the compounds described below have anti-oxidant action and accomplished the present invention.

The invention provides a method of preventing or treating a disease caused by oxidation in vivo by administering a pharmacologically effective amount of at least one compound selected from the group consisting of:

(1) 2,5,7.8-tetramethyl-2-(β-carboxyethyl)-6-hydroxychromane, a pharmacologically acceptable salt thereof or a pharmacologically acceptable hydrate thereof and (2) 2,7.8-trimethyl-2-(β-carboxyethyl)-6-hydroxychromane, a pharmacologically acceptable salt thereof or a pharmacologically acceptable hydrate thereof.

The invention then provides use of the compound as defined above (1) or (2) for manufacturing an anti-oxidant medicine.

The invention moreover provides use of a compound selected from the group consisting of (3) α-tocopherol, (4) α-tocotrienol, (5) γ-tocopherol and (6) γ-tocotrienol for generation in vivo of any of the compounds as above (1) and (2) to treat a disease caused by oxidated low density lipoprotein (LDL).

It is preferable that the disease is that caused by oxidated low density lipoprotein (LDL), especially being arteriosclerosis.

The present invention relates to antioxidants which are 2,5,7,8-tetramethyl-2-(β-carboxyethyl)-6-hydroxychromane or a salt thereof and/or 2,7,8-trimethyl-2-(β-carboxyethyl)-6-hydroxychromane, a salt thereof or a hydrate thereof. The present invention also relates to an antioxidant comprising 2,5,7,8-tetramethyl-2-(β-carboxyethyl)-6-hydroxychromane or a salt thereof and/or 2,7,8-trimethyl-2-(β-carboxyethyl)-6-hydroxychromane, a salt thereof or a hydrate thereof. The present invention also relates to an antioxidant comprising α-tocopherol and/or α-tocotrienol which exhibit anti-oxidant action when metabolized to 2,5,7,8-tetramethyl-2-(β-carboxyethyl)-6-hydroxychromane by metabolizing enzyme, or to an antioxidant comprising γ-tocopherol and/or γ-tocotrienol which exhibit anti-oxidant action when metabolized to 2,7,8-trimethyl-2-(β-carboxyethyl)-6-hydroxychromane by metabolizing enzyme. The present invention further relates to an agent for preventing or treating arterial sclerosis, which comprises 2,5,7,8-tetramethyl-2-(β-carboxyethyl)-6-hydroxychromane or a salt thereof and/or 2,7,8-trimethyl-2-(β-carboxyethyl)-6-hydroxychromane, a salt thereof or a hydrate thereof.

2,5,7,8-Tetramethyl-2-(β-carboxyethyl)-6-hydroxychromane according to the present invention is a metabolite of α-tocopherol or α-tocotrienol, which has the following formula (hereinafter referred to as "α-CEHC"). α-CEHC may also be referred to as 2,5,7,8-tetramethyl-2-(2'-carboxyethyl)-6-hydroxychromane.

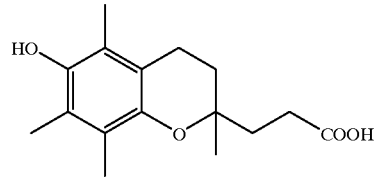

Further, 2,7,8-trimethyl-2-(β-carboxyethyl)-6-hydroxychromane is a metabolite of γ-tocopherol or γ-tocotrienol, which has the following formula (hereinafter referred to as "γ-CEHC"). γ-CEHC may also be referred to as 2,7,8-trimethyl-2-(2'-carboxyethyl)-6-hydroxychromane.

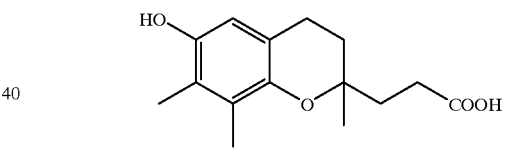

When α-CEHC and γ-CEHC are produced by metabolizing enzyme, optically active substance (S-configuration) may be produced. Racemic modifications thereof may be used in antioxidants or agents for preventing or treating arterial sclerosis according to the present invention.

α-CEHC and γ-CEHC may be prepared according to any known method. These compounds may be present in a form of salt combined with organic or inorganic material. Further, hydrates of these compounds or salts thereof may be used.

The effective amount of α-CEHC and/or γ-CEHC as antioxidants in blood may be, but not limited to, about 200 pmol/ml, for example. α-CEHC and/or γ-CEHC show antioxidant action not only in vivo but also when contained in pharmaceuticals, foods, diet and the like. α-CEHC or γ-CEHC may be used alone or in combination.

Alternatively, α-tocopherol, α-tocotrienol, γ-tocopherol or γ-tocotrienol itself may also exhibit in vivo anti-oxidant action after administration, since α-CEHC and γ-CEHC are produced by metabolisms of α-tocopherol, α-tocotrienol, γ-tocopherol or γ-tocotrienol in vivo. Conventionally, in vivo anti-oxidant activity has been confirmed in α-tocopherol but in α-tocotrienol, γ-tocopherol or γ-tocotrienol. The dosage of α-tocotrienol, γ-tocopherol or γ-tocotrienol required to obtain in vivo anti-oxidant action after oral administration is 10–2000 mg.

α-CEHC and/or γ-CEHC may be used as antioxidant directly or after formulated into any dosage form. Such formulation may be prepared by: mixing α-CEHC and/or γ-CEHC with an excipient such as lactose, mannitol and silicic acid anhydride, and then with a disintegrating agent (such as starch, low substitution hydroxypropylcellulose and crystalline cellulose) and a binder (such as hydroxypropyl cellulose, polyvinylpyrrolidone and hydroxypropylcellulose); granulating the mixture while adding solvent such as water and ethanol thereto; finely graining if necessary; and drying to form dry granules or fine granules. Further, such granules and the like may be formulated into capsules or tables, or dispersed into water to obtain liquid formulation. Optionally, organic solvent (e.g., ethanol), plant oil, synthetic oil, surfactant, flavors or the like may be added.

BRIEF DESCRIPTION OF THE DRAWING

FIG. 1 shows extended lag-times during which oxidization of LDL was inhibited by adding CEHC or the like.

EXPERIMENTAL EXAMPLE

Figure 1:
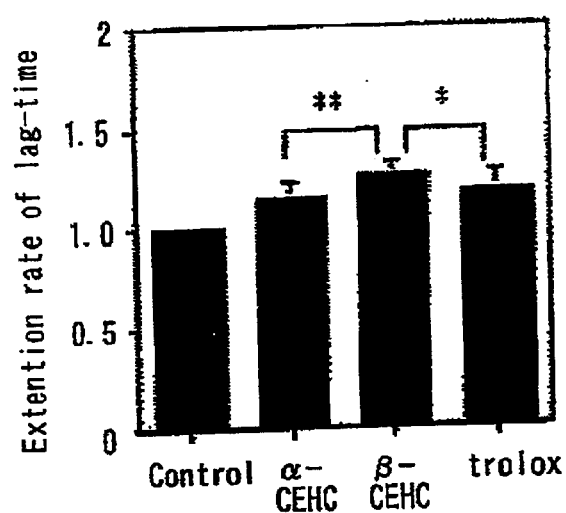

Compounds according to the present invention may have anti-oxidant action. They may be effective in vivo as an agent for preventing or treating arterial sclerosis. Hereinafter, effects of the compounds according to the present invention will be described in reference to the following Experimental Examples.
<Method>
1) Preparation of LDL Blood collected from human subject was centrifuged at 3000 rpm for 10 minutes to isolate plasma. Next, KBr was added to 1.1 mL of the plasma which was then subjected to density gradient ultra-centrifugation (Single spin differential centrifugation) to collect LDL. After the determination of protein concentration, LDL was prepared by PBS.
2) Oxidative Degeneration LDL Assay Using Azo-Compound (V-70)

In vitro assay of oxidatively denatured LDL was performed according to the method described by Kondo, et al. This method involves use of 2,2'-azobis(4-methyl-2,4-dimethylvaleronitrile; V-70) as the oxidation starter. Final concentration of V-70 was 200 $\mu$M for about 70 $\mu$g/mL of LDL protein concentration, and production of the conjugate dienes of LDL was assayed at 234 nm for 300 minutes. The time during which conjugate diene production was inhibited was indicated as lag-time. The efficacy of each antioxidants was evaluated by adding the compound and V-70 at the same time and determining the lag-time caused by the compound.
Results
1) Anti-Oxidative Effects of α- and γ-CEHCs on LDL At first, α- or γ-CEHCs was added to LDL concentration-dependently (final concentration: 60–1000 ng) and their anti-oxidative activities were examined. The results showed prolonged lag-times concentration-dependently for both α- and γ-CEHCS. Thus, it was shown that both of α- and γ-CEHCs have anti-oxidative effects also on LDL.

2) Comparison of Anti-Oxidative Effects on LDL Between CEHCS and Trolox (at Higher Concentration)

Comparison with trolox (a water-soluble synthetic antioxidant) was performed. Blood was collected from eight male and female adults, and LDL was collected therefrom according to the above-described method. Then, α-CEHC, γ-CEHC or trolox was added to the LDL (at final concentration: 1 $\mu$g) and lag-time was determined. Control group without antioxidant showed lag-time of 88.1±29.4 minutes while the group added with α-CEHC showed significantly prolonged lag-time of 190.8±65.1 minutes (p<0.01). Further, the group added with γ-CEHC showed lag-time of 263.1±114.8 minutes which was significantly longer than that of α-CEHC group. Thus, γ-CEHC had significantly stronger anti-oxidative effects on LDL than α-CEHC did.
3) Comparison of Anti-Oxidative Effects on LDL Between CEHCs and Trolox (at Lower Concentration)

Stahl, et al., (Anal. Biochem, 275, 254–259, 1999) reported that plasma α-CEHC concentration was 200 pmol/mL when 500IU RRR-α-tocopherol was administered to human subject and that most of γ-CEHC derived from γ-tocopherol were present in a free state when taken with foods. Therefore, its anti-oxidative effect on LDL was also examined, with the concentration at which it can be present in plasma. Control group was also prepared by adding Trolox in the same manner as described above and the final concentration was set close to 200 pmol/mL described above (final concentration: 60 ng) for comparison.

Results are shown in FIG. 1. In the drawing, control group is indicated by 1, and extension rates of lag-times are shown. As seen in FIG. 1, γ-CEHC group had a greater increase in extension rate of lag-time than those of α-CEHC and Trolox groups. Thus, it was proved that not only tocopherol but also CEHCs (particularly γ-CEHC) may be very efficient anti-oxidants in plasma and exhibit anti-oxidative effect on LDL membrane surface. Further, since it was shown that metabolites of vitamin E (particularly γ-tocopherol and γ-tocotrienol) have such biological activities, it can be assumed that strong vitamin E efficacy may possibly be obtained in treatment of arterial sclerosis and heart disease by administering γ-tocopherol and/or γ-tocopherol at the same time.

What is claimed is:

1. A method of treating a disease caused by oxidation in vivo, said method comprising a step of administering a pharmacologically effective amount of a compound selected from the group consisting of:

(1) 2,5,7,8-tetramethyl-2-(β-carboxyethyl)-6-hydroxychromane, a pharmacologically acceptable salt thereof, or a pharmacologically acceptable hydrate thereof; and (2) 2,7,8-trimethyl-2-(β-carboxyethyl)-6-hydroxychromane, a pharmacologically acceptable salt thereof, or a pharmacologically acceptable hydrate thereof;

wherein said disease is selected from the group consisting of arteriosclerosis and heart disease.

2. The method according to claim 1, wherein said disease is caused by oxidated low density lipoprotein (LDL).

* * * * *